United States Patent
Wu et al.

(10) Patent No.: US 10,694,959 B2
(45) Date of Patent: Jun. 30, 2020

(54) IMAGE BASED BLOOD PRESSURE MONITORING METHOD

(71) Applicant: National Chiao Tung University, Hsinchu (TW)

(72) Inventors: Bing-Fei Wu, Hsinchu (TW); Po-Wei Huang, Hsinchu (TW); Chun-Hao Lin, Hsinchu (TW); Meng-Liang Chung, Hsinchu (TW); Tzu-Min Lin, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 104 days.

(21) Appl. No.: 16/040,660

(22) Filed: Jul. 20, 2018

(65) Prior Publication Data

US 2019/0246917 A1    Aug. 15, 2019

Related U.S. Application Data

(60) Provisional application No. 62/629,945, filed on Feb. 13, 2018.

(51) Int. Cl.
G06K 9/00 (2006.01)
A61B 5/024 (2006.01)
(Continued)

(52) U.S. Cl.
CPC ........ *A61B 5/02416* (2013.01); *A61B 5/0013* (2013.01); *A61B 5/0077* (2013.01); *A61B 5/024* (2013.01); *A61B 5/02125* (2013.01); *A61B 5/7203* (2013.01); *A61B 5/726* (2013.01); *A61B 5/7257* (2013.01); *A61B 5/7264* (2013.01); *A61B 5/7275* (2013.01); *A61B 5/7278* (2013.01); *A61B 5/7485* (2013.01); *G06F 3/017* (2013.01); *G06K 9/00302* (2013.01);
(Continued)

(58) Field of Classification Search
None
See application file for complete search history.

(56) References Cited

U.S. PATENT DOCUMENTS 6,475,153 B1 * 11/2002 Khair ............... A61B 5/02007
                                                    600/485
2008/0045847 A1 * 2/2008 Farag ............... A61B 5/02055
                                                    600/500
(Continued)

OTHER PUBLICATIONS

Bing-Fei Wu et al., "Camera-based Heart Rate Measurement Using Continuous Wavelet Transform", Jul. 21-23, 2017, IEEE.
(Continued)

*Primary Examiner* — Shervin K Nakhjavan
(74) *Attorney, Agent, or Firm* — Bacon & Thomas, PLLC

(57) ABSTRACT

The present invention provides an image based blood pressure monitoring method, comprising: acquiring at least a human image information of at least a human skin area; according to the human image information to locate at least a ROI; extracting the human image information of the ROI, and calculate; filtering the average value of the human image information; monitoring the filtered signal; calculating an image pulse transmit time of the filtered signal, and calculating an inter-beat interval of the filtered signal; and employ the specific prediction model, to calculate a systolic pressure value and a diastolic pressure value.

10 Claims, 4 Drawing Sheets

(51) Int. Cl.
    *A61B 5/00*    (2006.01)
    *G06F 3/01*    (2006.01)
    *A61B 5/021*   (2006.01)
    *G06T 7/246*   (2017.01)
    *A61B 5/0402*  (2006.01)
    *G06T 7/20*    (2017.01)

(52) U.S. Cl.
    CPC .............. *A61B 5/0402* (2013.01); *A61B 5/725* (2013.01); *A61B 5/7207* (2013.01); *A61B 2576/00* (2013.01); *G06T 7/20* (2013.01); *G06T 7/246* (2017.01)

(56) References Cited

U.S. PATENT DOCUMENTS

| | | | | | |
|---|---|---|---|---|---|
| 2013/0331669 | A1* | 12/2013 | Berte | ................. | G06T 7/0016 600/324 |
| 2013/0331700 | A1* | 12/2013 | Kawabata | ............ | A61B 8/0858 600/443 |
| 2013/0345569 | A1* | 12/2013 | Mestha | ................. | A61B 5/0044 600/473 |
| 2015/0257653 | A1* | 9/2015 | Hyde | .................... | A61B 5/021 600/473 |
| 2016/0106327 | A1* | 4/2016 | Yoon | ................... | A61B 5/02108 600/480 |
| 2017/0164904 | A1* | 6/2017 | Kirenko | ............... | A61B 5/7214 |
| 2017/0245768 | A1* | 8/2017 | White | ................ | G06K 9/00496 |
| 2018/0199870 | A1* | 7/2018 | Lee | ......................... | G16H 40/63 |
| 2019/0060602 | A1* | 2/2019 | Tran | ........................ | A61B 34/10 |
| 2019/0167118 | A1* | 6/2019 | Vilenskii | ............. | A61B 5/0059 |

OTHER PUBLICATIONS

Po-Wei Huang et al., "Image Based Contactless Blood Pressure Assessment using Pulse Transit Time", Nov. 12-15, 2017, The 2017 International Automatic Control Conference (CACS 2017),IEEE.

Bing-Fei Wu et al., "A contactless sport training monitor based on facial expression and remote-PPG", Oct. 5-8, 2017, IEEE.

* cited by examiner

IMAGE BASED BLOOD PRESSURE MONITORING METHOD

BACKGROUND OF THE INVENTION

1. Field of the Invention

The present invention relates to an image based blood pressure monitoring method, particularly to a method of using an image method to monitor the blood pressure, and no need to contact human body directly.

2. Description of the Prior Art

In the conventional techniques, the common physiological monitoring instruments for measuring the health state of testee need to use wire to connect the sensor to the body of testee generally. With a long time, it is quite uncomfortable and inconvenient. However, as for contactless monitoring device, the price is very high and hard to obtain, which will not be suitable to be used at home or by the individual person.

With the gradual progress of mobile operation method, the efficiency of intelligent handheld device becomes better and better. In order to make the pulse measurement more convenient and more comfortable, in fact, the application program has been developed on the intelligent handheld device at present, to achieve the use of contactless image pulse measurement method.

In the abovementioned technique, the user needs not to wear any sensor again. Only need to place the intelligent handheld device on face or palm of user, it will be able to start tracking the region of interest (ROI) in the face image. That is, to use the camera to spot the variation of image luminance on human skin, and then extract the image in the region of interest as the signal.

Recent years have seen increased attention been given to pulse monitoring. Among all kinds of measurements, the monitoring way based on pulse transit time (PTT) have gain plenty of attention due to its continuous and non-touch features. In addition, several studies proposed a fancy method to estimate photoplethysmography (PPG) signal simply via a regular webcam, in order to finish pulse monitoring.

For most testees, the difficulty in regular home pulse measurement may result from the bulky and uncomfortable measuring process. Up to present, commonly used pulse monitors can be classified into the following three classes:
 (a) invasive and continuous monitoring;
 (b) noninvasive and intermittent monitoring; and
 (c) noninvasive and continuous monitoring.

Firstly, with invasive arterial line, (a) invasive and continuous pulse monitors can measure pulse most accurately. Nonetheless apart from the specific requirement for equipment, the stabbing pain of acupuncture makes this technique difficult to be accepted by patients.

Secondly, type of (b) noninvasive and intermittent monitor frequently utilizes stethoscope or mercury sphygmomanometer or electronic sphygmomanometer. Although these devices are not invasive and easy to use, an inflatable cuff in necessary, which may give rise to discomfort of arm during measurement. Additionally, devices based on these two principles can only provide intermittent measurement.

Lastly (c) noninvasive and continuous monitors are commonly developed using the volume clamp method or plus transit time (PTT), which have gain plenty of attention. However, the clamp may bring about discomfort and the accuracy may be controversial.

To address the abovementioned problems, it is necessary to develop a contactless monitoring technique, to display the wave form value of pulse real time, and monitor the amplitude frequency phase of testee's pulse, and sense the micro topographical variation of body remotely.

SUMMARY OF THE INVENTION

The embodiment of the present invention provides an image based blood pressure monitoring method, comprising: acquiring at least a human image information of at least a human skin area, to obtain a human image information; according to the human image information to locate at least a Region of Interest (ROI); extracting the human image information of the Region of Interest (ROI), and calculate to obtain an average value of the human image information; filtering the average value of the human image information, to remove the noise in order to obtain a filtered signal; detecting the filtered signal, to obtain a plural of feature points of the filtered signal; calculating an image pulse transmit time of the filtered signal, and calculating an inter-beat interval of the filtered signal; and employ prediction model, which could be k-nearest neighbor (kNN) or neural net model, accord with the specific time interval, which could be image pulse transit time (iPTT) and inter-beat interval (IBI), as the input parameters, to calculate a systolic pressure (SBP) value and a diastolic pressure value, wherein when said systolic pressure (SBP) value is smaller than specific lower bound or greater than specific higher bound, said systolic pressure (SBP) value will be removed.

In the aforesaid preferred embodiment, the human image information is a color image, the average value of human image information is a combination of single-channel or multi-channels average value, which includes but not limited to g-Trace, a green channel average value.

In the aforesaid preferred embodiment, the steps for the k-nearest neighbor prediction model according to the calculate the specific time interval including image Pulse Transit Time and the inter-beat interval to calculate the systolic pressure value and the diastolic pressure value further include a transfer learning of the k-nearest neighbor prediction model based on a MIMIC II database.

In the aforesaid preferred embodiment, which further comprises when the systolic pressure value is smaller than 80 mmHg or greater than 190 mmHg, the systolic pressure value will be removed. Thus, wherein, the specific lower bound ranges from 60 mmHg to 90 mmHg and the specific higher bound ranges from 170 mmHg to 210 mmHg respectively.

In the aforesaid preferred embodiment, which further comprises when the diastolic pressure value is smaller than 50 mmHg or greater than 120 mmHg, the diastolic pressure value will be removed.

In the aforesaid preferred embodiment, the steps for the transfer learning of k-nearest neighbor prediction model based on a MIMIC II database further comprise: making the distribution of systolic pressure value and diastolic pressure value consistent through the multiple-scale entropy (MSE); and eliminating the image Pulse Transit Time with bias and variation through the standard score (Z-score).

In the aforesaid preferred embodiment, the region of interest (ROI) is the skin region of palm and face.

In the aforesaid preferred embodiment, a finite impulse response (FIR) filter is employed to filter the noise for the average value of the image information.

In the aforesaid preferred embodiment, the cut-off frequency of the finite impulse response filter is 45 bpm to 180 bpm.

In the aforesaid preferred embodiment, the inter-beat interval (IBI) can be used to calculate the heart rate value.

In order to further understand the features and technological content of the present invention, please refer to the following detailed description and attached figures of the present invention. Nevertheless, the attached figures are used for reference and description, which are not used for limiting the present invention.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

In the following context, the specific embodiments are used to describe the image based blood pressure monitoring method of the present invention. The people who are familiar to this art can understand the advantages and efficacies of the present invention easily from the content disclosed in this article. The present invention can also be implemented or applied by other different embodiments. Every detail in this article can also be modified and changed based on different viewpoints and applications without violating the spirit of the present invention. In addition, the figures in the present invention are only brief description, and they are not drawn in actual dimension to reflect the actual size. The following description of preferred embodiment describes the viewpoint of the present invention in more detail, which will not limit the scope of the present invention by any viewpoint.

Figure 1:
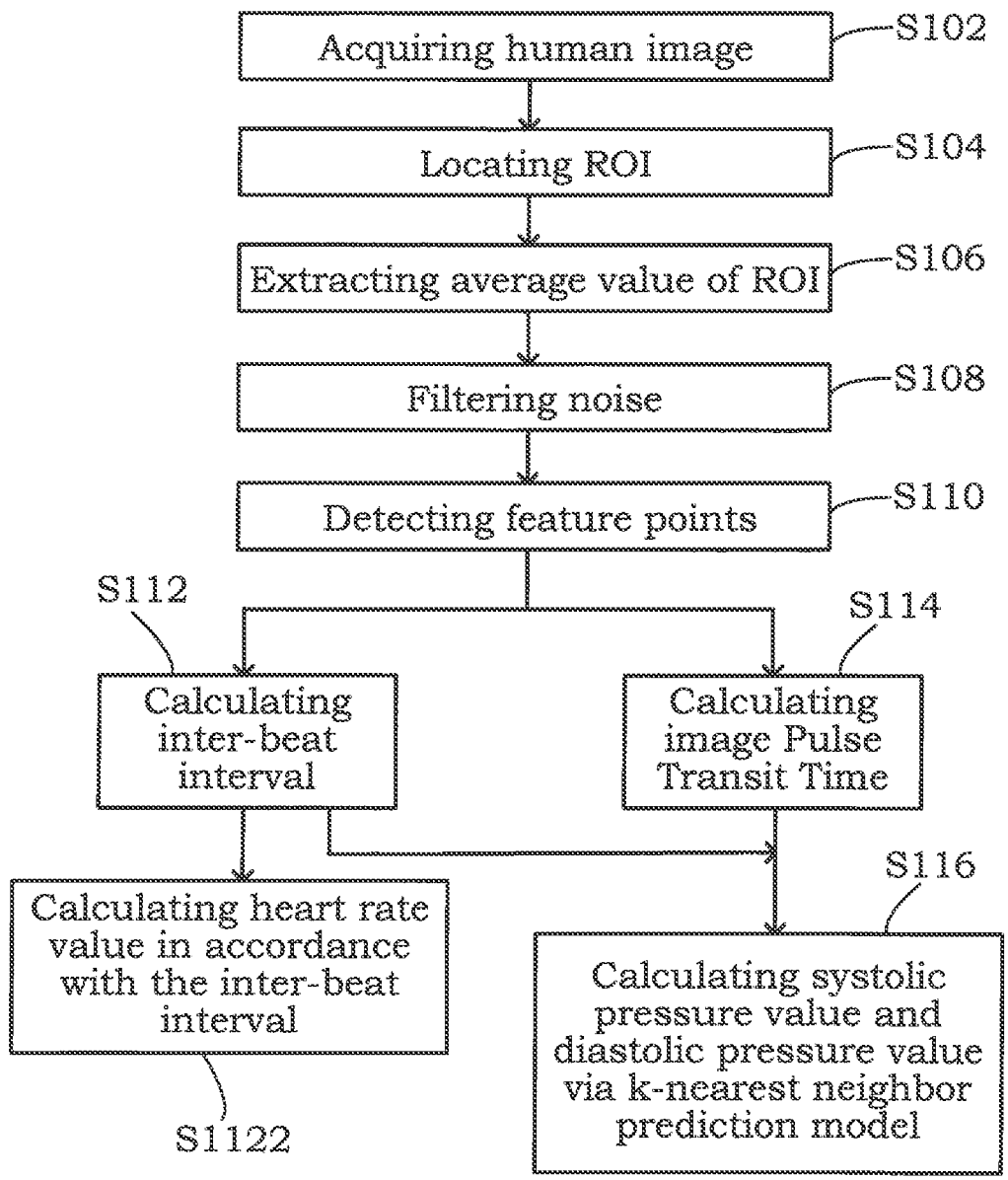
FIG. 1 illustrates a flowchart of image based blood pressure monitoring method of the present invention.
Figure 2:
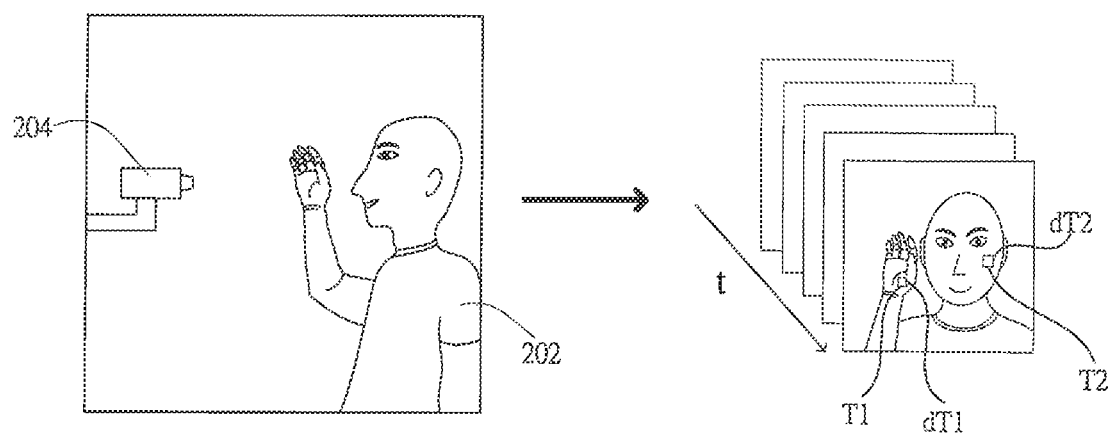
FIG. 2 illustrates an image based blood pressure monitoring device of the present invention.

Please refer to FIG. 1 and FIG. 2. FIG. 1 illustrates a flowchart of image based blood pressure monitoring method of the present invention, and FIG. 2 illustrates an image based blood pressure monitoring device of the present invention.

The image based blood pressure monitoring method of the present invention comprises the following steps of FIG. 1 and FIG. 2. As shown in FIG. 2, the image acquisition unit 204 takes the image of human body 202, and the image acquisition unit 204 tracks at least a region of interest (ROI) T1 (or a target image T2 in ROI dT2) in human image information dT1.

As shown in Step S102 of FIG. 1, use the image acquisition unit 204 to acquire the image of skin region of human body 202, acquire at least a human image to obtain a human image information.

As shown in Step S104 of FIG. 1, according to the human image information locate at least a ROI. In the embodiment, the ROI is face ROI dT2 and palm ROI dT1. The ROI of the present invention is not limited to these parts, which can be any exposed skin of human body.

As shown in Step S106 of FIG. 1, extract the human image information of the ROI, and calculate an average value of the human image information.

As shown in FIG. 2, acquire the palm image information T1 of the palm ROI dT1 and the face image information T2 of the face ROI dT2, respectively. The palm ROI dT1 and the face ROI dT2 is a region with 20×20 pixels.

In the embodiment of the present invention, the human image information is a color image. Because a small fraction of incident light (<5%) will be absorbed by the microvascular network, the variation of blood capacity can be monitored through monitoring the pulse signal via the image acquisition unit 204. In addition, in the three color channels composed of the image, the highest ac/dc ratio in light reflected from skin can be obtained via the color variation of g-Trace. Thus, the g-Trace of palm ROI dT1 and face ROI dT2 is used as the tracking value. Although the quantization noise is preliminary filtered after taking the average of each frame, there are still some other sources of noise (e.g. motion of subject, variation of ambient light). The average value of the human image information is a combination of single-channel or multi-channels average value, which includes but not limited to g-Trace.

In Step S102 to Step S108 of FIG. 1, it shows the image photoplethysmography (iPPG) signal recovery method of the present invention.

Figure 3:
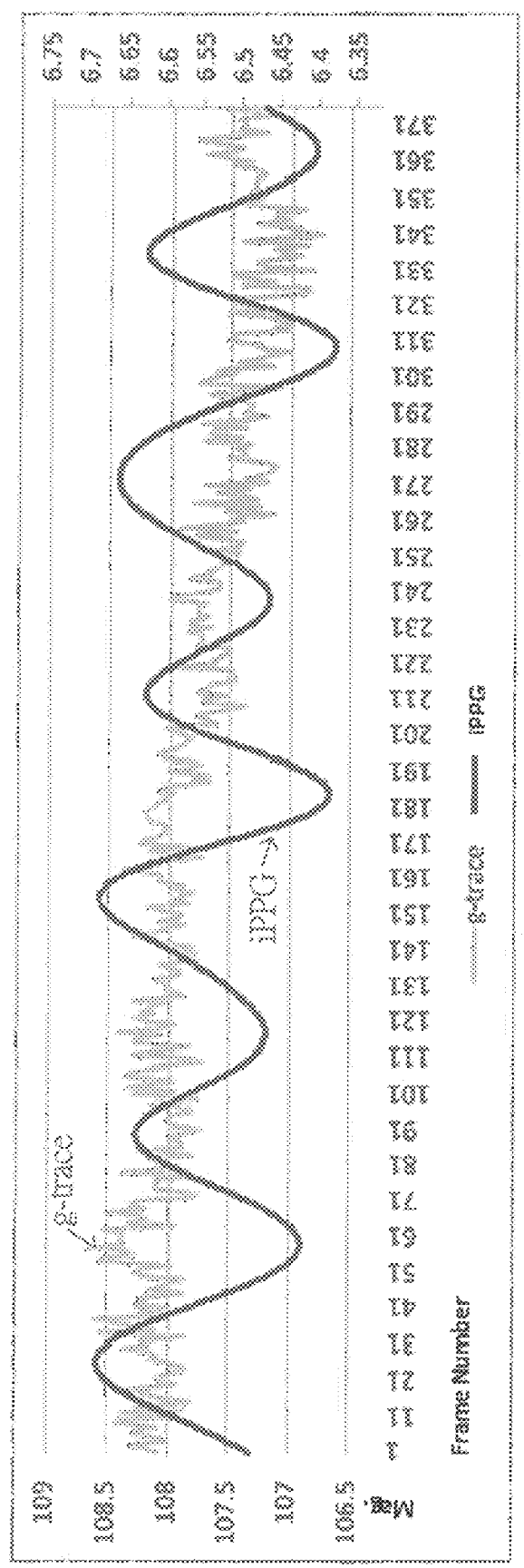
FIG. 3 illustrates the green channel average value (g-Trace) and the filtered signal (F1 or F2) of the present invention.

As shown in Step S108 of FIG. 1, a signal enhancement filter, which could be a finite impulse response filter, is used to filter the average value of palm image information T1 and face image information T2, respectively. The noise of palm image information T1 and face image information T2 is filtered, to obtain the palm filtered signal F1 and the face filtered signal F2. The cut-off frequency of finite impulse response filter is 45 bpm to 180 bpm, as shown in FIG. 3. It is known that FIG. 3 illustrates the green channel average value (g-Trace) and the filtered signal (F1 or F2) of the present invention.

Figure 4:
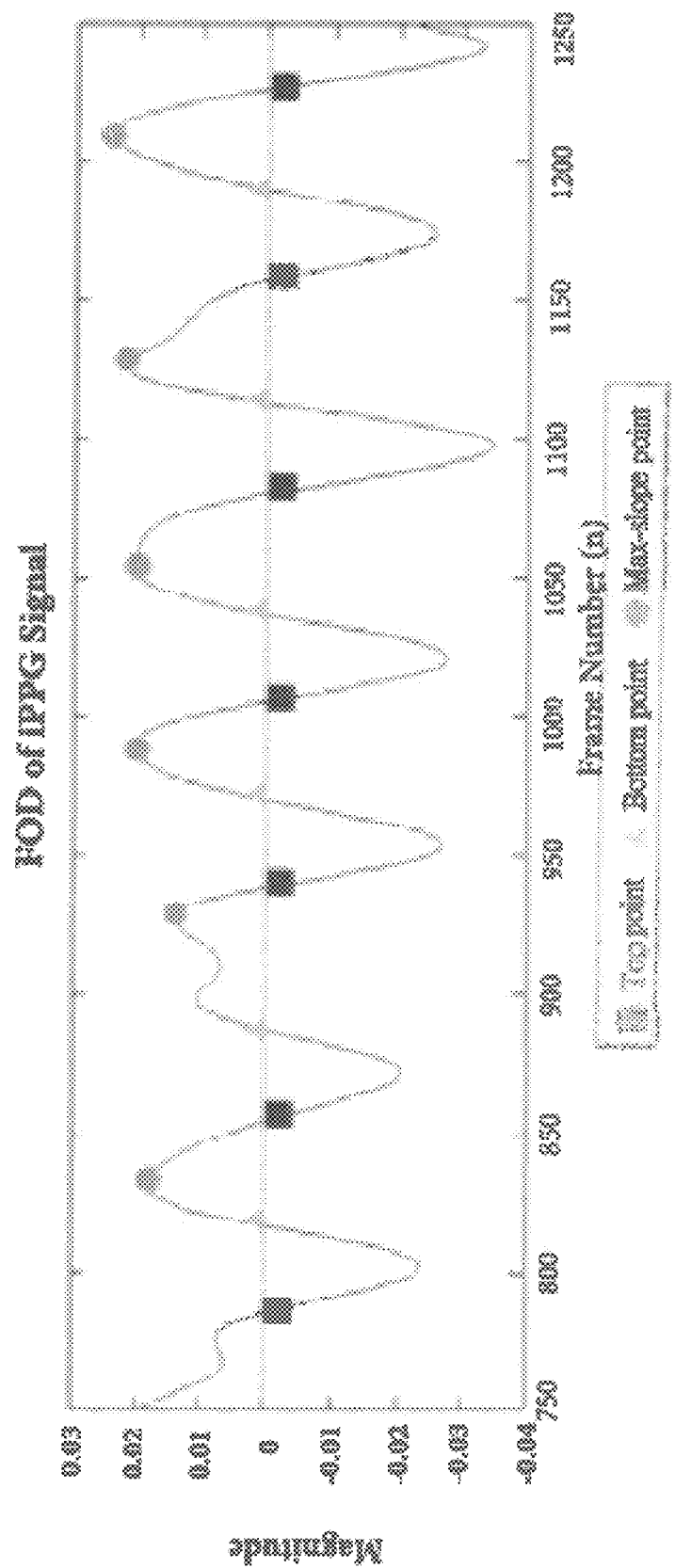
FIG. 4 illustrates the feature points of the present invention.

As shown in Step S110 of FIG. 1, detect the filtered signal to obtain a plural of feature points of the filtered signal. The feature points are obtained from making a differential analysis of palm filtered signal F1 and face filtered signal F2, as shown in FIG. 4. It is known that FIG. 4 illustrates the feature points of the present invention.

In Step S112 of FIG. 1, calculate the specific time interval, which includes but not limited to image pulse transit time (iPTT) of filtered signal, or the inter-beat interval (IBI) of filtered signal.

In Step S114 of FIG. 1, calculate an image pulse transit time (iPTT) of filtered signal, and calculate an inter-beat interval (IBI) of filtered signal.

In Step S116 of FIG. 1, employ the specific prediction model, which includes but not limited to k-nearest neighbor (kNN) or neural net model, accord with the image pulse transit time (iPTT) and inter-beat interval (IBI) as the input parameters, to calculate a systolic pressure value and a diastolic pressure value, wherein when said systolic pressure (SBP) value is smaller than specific lower bound or greater than specific higher bound, said systolic pressure (SBP) value will be removed.

In an preferred embodiment of the present invention, in Step S116 of FIG. 1 for employing the k-nearest neighbor (kNN) prediction model, and according with the image pulse transit time (iPTT) and inter-beat interval (IBI) as the input parameters, to calculate a systolic pressure (SBP) value and a diastolic pressure (DBP) value, which further comprises that the k-nearest neighbor method (kNN) prediction model uses a MIMIC II database as a basis to carry on a transfer learning. It has to note that the MIMIC II database is one of the biggest physiological databases in the world. The information comprises: surgery, neonate, and coronary artery care etc. In the present invention, the palm signal (PPG), face signal (ABP) and electro-cardiogram signal (ECG) can be utilized.

In Step S116 of FIG. 1, in order to remove the abnormal value from the collected information, when the systolic pressure (SBP) value is smaller than specific lower bound, 80 mmHg, or greater than specific higher bound, 190 mmHg, the SBP value will be removed, and when the diastolic pressure (DBP) value is smaller than specific lower bound, 50 mmHg, or greater than specific higher bound, 120 mmHg, the DBP will be removed. Thus, wherein, wherein said specific lower bound ranges from 40 mmHg to 60 mmHg and said specific higher bound ranges from 110 mmHg to 130 mmHg respectively.

In Step S116 of FIG. 1, the steps for the transfer learning of k-nearest neighbor prediction model based on a MIMIC II database further comprises:

In Step S116 of FIG. 1, making the distribution of systolic pressure (SBP) value and diastolic pressure (DBP) value consistent through the multiple-scale entropy (MSE); and eliminating the image pulse transit time (PTT) with bias and variation through the standard score (Z-score). Upon using the MIMIC II database, it is unable to obtain the measured palm signal (PPG), face signal (ABP). In addition, the pulse transmit time will have great difference due to different position of signal source. Although the absolute pulse transmit time between two domains is completely different, a shorter PTT will display higher BP. It is to say consuming time still has some meaning, and only the bias in different domain can be eliminated. In view of this, the standard score (Z-score) can be utilized to eliminate the influence of bias on each feature.

In another embodiment of the present invention, after Step S112 of FIG. 1, it further comprises Step S1122, wherein the heart rate (HR) value can be calculated in accordance with the inter-beat interval (IBI).

It is understood that various other modifications will be apparent to and can be readily made by those skilled in the art without departing from the scope and spirit of the invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which the invention pertains.

What is claimed is:

1. an image based blood pressure monitoring method, comprising:

acquiring at least a human image information of at least a human skin area, to obtain a human image information;

according to said human image information to locate at least a region of interest (ROI);

extracting the human image information of said ROI, and calculate to obtain an average value of said human image information;

filtering said average value of said human image information, to remove a noise in order to obtain a filtered signal;

detecting said filtered signal, to obtain a plural of feature points of said filtered signal;

calculating an specific time interval of said filtered signal; and employ a specific prediction model, according with said specific time interval as an input parameters, to calculate a systolic pressure (SBP) value and a diastolic pressure (DBP) value.

2. The image based blood pressure monitoring method according to claim 1, wherein said human image information is a color image, said average value of said human image information as a combination of single-channel or multi-channels average value.

3. The image based blood pressure monitoring method according to claim 1, wherein said specific prediction model utilized comprises a k-nearest neighbor predictor.

4. The image based blood pressure monitoring method according to claim 3, wherein which further comprises when said diastolic pressure (DBP) value is smaller than specific lower bound or greater than specific higher bound, said diastolic pressure (DBP) value will be removed.

5. The image based blood pressure monitoring method according to claim 4, wherein said specific lower bound ranges from 40 mmHg to 60 mmHg and said specific higher bound ranges from 110 mmHg to 130 mmHg respectively.

6. The image based blood pressure monitoring method according to claim 1, wherein said specific prediction model utilized comprises a neural net predictor.

7. The image based blood pressure monitoring method according to claim 1, wherein said specific time interval comprises obtained pulse transit time.

8. The image based blood pressure monitoring method according to claim 1, wherein said specific time interval obtained comprises an inter-beat interval.

9. The image based blood pressure monitoring method according to claim 1, wherein when said systolic pressure (SBP) value is smaller than specific lower bound or greater than specific higher bound, said systolic pressure (SBP) value will be removed.

10. The image based blood pressure monitoring method according to claim 9, wherein said specific lower bound ranges from 60 mmHg to 90 mmHg and said specific higher bound ranges from 170 mmHg to 210 mmHg respectively.

* * * * *